(12) United States Patent
Buccellato (10) Patent No.: US 6,328,935 B1
(45) Date of Patent: Dec. 11, 2001

(54) AROMA DISPENSER FOR CANDLE

(75) Inventor: Felix Buccellato, Belle Mead, NJ (US)

(73) Assignee: Custom Essence, Inc., Somerset, NJ (US)

( * ) Notice: Subject to any disclaimer, the term of this patent is extended or adjusted under 35 U.S.C. 154(b) by 0 days.

(21) Appl. No.: 09/610,825

(22) Filed: Jul. 6, 2000

(51) Int. Cl.⁷ ...................................................... A62B 7/08
(52) U.S. Cl. ............................. 422/125; 422/5; 422/123; 422/125; 431/320; 431/321; 431/322; 431/323; 431/324
(58) Field of Search .................. 422/5, 123, 125; 431/320, 321, 322, 323, 324

(56) References Cited

U.S. PATENT DOCUMENTS

| | | | |
|---|---|---|---|
| 2,254,906 | 9/1941 | Petrulis | 21/117 |
| 2,323,804 | 7/1943 | Driscoll | 167/41 |
| 2,668,993 | * 2/1954 | Bair | 422/125 |
| 3,175,876 | 3/1965 | Fredericks | 21/116 |
| 3,615,289 | 10/1971 | Felton | 44/7.5 |
| 3,898,039 | 8/1975 | Lin | 21/108 |
| 3,948,445 | * 4/1976 | Andeweg | 422/125 |
| 3,958,917 | 5/1976 | Naz | 431/289 |
| 4,054,636 | 10/1977 | Menig | 264/250 |
| 4,110,261 | 8/1978 | Newland | 252/522 |
| 4,427,366 | 1/1984 | Moore | 431/291 |
| 4,568,270 | 2/1986 | Marcus et al. | 431/288 |
| 4,614,625 | 9/1986 | Wilson | 264/6 |
| 4,663,315 | * 5/1987 | Hasegawa et al. | 514/86 |
| 4,708,851 | * 11/1987 | Freytag Von Loringhaven | 422/125 |
| 4,781,895 | * 11/1988 | Spector | 422/125 |
| 4,826,428 | 5/1989 | Lam | 431/291 |
| 5,127,825 | * 7/1992 | Tendick, Sr. | 431/320 |
| 5,827,483 | * 10/1998 | Fullam | 422/125 |
| 5,840,246 | * 11/1998 | Hammons et al. | 422/125 |
| 5,871,553 | 2/1999 | Spaulding | 44/275 |
| 5,955,034 | 9/1999 | Zaunbrecher et al. | 422/126 |
| 5,964,905 | 10/1999 | Camp et al. | 44/275 |
| 6,013,231 | 1/2000 | Zaunbrecher et al. | 422/126 |

* cited by examiner

Primary Examiner—Robert J. Warden, Sr.
Assistant Examiner—Imad Soubra
(74) Attorney, Agent, or Firm—Kenneth Watov; Watov & Kipnes, P.C.

(57) ABSTRACT

An aroma dispenser comprises a flame source for providing heat, an open, porous annular ceramic substrate adapted for absorbing and reversibly retaining a quantity of at least one aromatic fluid therein, a support structure for holding the porous substrate in a coaxial spaced-apart relationship above the flame source, whereby heat generated by the flame source induces the retained aromatic fluid within the substrate to disperse into the ambient air.

22 Claims, 7 Drawing Sheets

AROMA DISPENSER FOR CANDLE

FIELD OF THE INVENTION

The present invention relates generally to an aroma dispensing device, and more particularly to a device for dispensing aroma by candle heat.

BACKGROUND OF THE INVENTION

Scented wax candles have been widely used in many places for dispensing aromatic scent into the air. Such candles are typically made by blending melted wax material with an aromatic substance. When thoroughly blended, the resulting aromatic mixture is poured into a mold. The poured wax mixture then cools into a solid form with a fiber wick enclosed therein for a candle. Alternatively, the mixture may be poured into a permanent container or glass holder for forming an enclosed candle. When the wick of the candle is lit for use, the heat gradually melts the wax adjacent to the wick and releases some of the fixed aromatic substance in the form of vapors. The released vapors disperse into the air for furnishing a pleasant aroma within a small, enclosed area.

Although scented wax candles are commonly used as aroma dispensers, such candles are generally inefficient and inadequate for such purposes. During use, most of the heat generated by the candle flame travels upwardly away from the wax portion of the candle below. Accordingly, very little of the heat is available to drive the aromatic substances out of the melted wax. Moreover, melted candle wax possesses a tendency to substantially reduce the vapor pressure of the aromatic substances contained therein. Thus, only a minute portion of the aromatic content is actually released from the candle into the air. The vast portion of the aromatic substance remaining is simply carried up the wick with the melted wax and undesirably combusted into non-fragrant by-products.

Scented wax candles also possess a limited shelf life. Candle wax is a porous substance with poor fluid retaining attributes. Thus, any aromatic substance contained therein will slowly diffuse out through the wax composition over time. This further reduces the aromatic content of the candle available for dispersing. Significant losses of aromatic substances also may also occur during the manufacturing process. Since the aromatic substance is typically added to the wax in its hot melted form, a considerable amount is vaporized and dispersed during the mixing, pouring, molding and cooling operations before the substance becomes fixed in the cooled solid wax.

Another disadvantage observed with scented wax candles is the tendency of the candle wax and the aromatic substance to undesirably interact with each other. For example some candle wax compositions may negatively alter the aromatic substance's physical and chemical properties. Such undesirable changes may result in the suppression of aromas and/or the output of undesirable odors or vapors. Moreover, some aromatic substances can discolor or adversely affect the structure and other desirable properties of the candle wax composition, thus producing an inferior product. Such undesirable chemical interaction and interference greatly diminishes the aroma dispensing efficacy of the scented wax candles.

It is understood that once the aromatic substance is added to the wax composition, the amount and type of the aromatic substance added cannot be easily altered or changed. Individual taste with respect to a particular aroma is often variable and subject to wane during the expected life of a scented wax candle. The rate at which the candle dispenses the aroma is likewise fixed and substantially constant. Thus, if during the course of a candle's life the user's tastes change, the only option is to set the old candle aside and acquire a new candle with the new particularly desired aroma. In addition, many users prefer to mix different aromatic substances to form a personalized "aroma recipe." With scented wax candles, such an option is not available to the user. Accordingly, scented wax candles undesirably lack flexibility and versatility in use as aroma dispensers.

One prior art aroma dispenser is a non-candle aroma dispensing device manufactured by "Delightful Scents" under the name of "Light Bulb Fragrance Ring." The device includes a ceramic annulus with a reservoir extending along a top portion thereof. The ceramic annulus is adapted to receive into the reservoir a quantity of an aromatic substance, and adapted to mount directly on a standard incandescent light bulb. The heat given off by the light bulb causes the aromatic substance to vaporize and diffuse into the air. The device permits the user to select a desired aromatic substance for use. However, such devices poses several hazards and limitations. The temperature of a typical incandescent light bulb can reach to at least 5,400° F. at the filament. Since some aromatic substances may be flammable, direct contact of the hot light bulb with the ceramic annulus and the aromatic substance may ignite the latter, thereby creating a dangerous fire hazard. Typical incandescent lamps are further configured to include an electrical light socket which is located below the light bulb. Since liquid aromatic substances are preferably used, such devices may further pose an electrical shock hazard should some of the substance leak down the bulb and into the socket. There is also the danger that the ceramic annulus may break the glass bulb if their respective thermal expansion coefficients are not closely matched.

For the foregoing reasons, there is a need for an improved aroma dispenser for use with candles that permits the user to easily change the type and rate or strength of aroma for dispensing as desired. It would be a significant advance in the art of aroma dispensing to develop an aroma dispenser for use with lit candles, which efficiently provides pleasant aromas in a safe manner, while being inexpensive and easy to use.

SUMMARY OF THE INVENTION

The present invention is generally directed to the combination of an aroma dispenser with a candle for providing light and heat. The aroma dispenser includes means for retaining and dispensing an aromatic fluid in a manner which provides the benefits of an efficient and an effective air freshener with the flexibility and advantages allowing the user to select and change to any desired aroma, and to adjust the aroma delivery rate into the ambient air through use of an associated lit candle. The aroma dispenser generally comprises an open, porous substrate for absorbing and reversibly retaining a quantity of at least one aromatic fluid in a safe and clean manner. The aromatic fluid being retained within the substrate, disperses in a vaporous form into the ambient air when heated by a candle flame. Alternatively, the substrate can be used to efficiently deliver fragrance at lower levels when the candle is not lit.

In particular, one aspect of the present invention is directed to an aroma dispenser which comprises:
 a) a flame source consisting of a candle;
 b) an open, porous substrate adapted for absorbing and reversibly retaining a quantity of at least one aromatic fluid therein; and c) a support structure for holding the porous substrate in a spaced-apart relationship above from the candle, whereby heat generated by the lit candle induces the retained aromatic fluid within the substrate to disperse into the ambient air.

BRIEF DESCRIPTION OF THE DRAWINGS

Various embodiments of the invention are described in detail below with reference to the drawings, in which like items are identified by the same reference designation, wherein.

DETAILED DESCRIPTION OF THE INVENTION

The present invention is generally directed to an aroma dispenser constructed in a manner to provide a simple and inexpensive arrangement for dispersing a quantity of an aromatic or scent-producing fluid into ambient air. The aroma dispenser provides for a candle with a wick and a support structure for supporting a porous substrate. The support structure retains the porous substrate in a position above and in close proximity to the candle wick. The porous substrate is configured to absorb and reversibly retain a quantity of an aromatic fluid therein. Through evaporative effects induced by ambient heat and/or heat generated by the lit candle for accelerating evaporation, the aromatic fluid is converted into vapors which diffuse into the ambient air for a pleasant aroma.

The aroma dispenser is constructed with the advantage of permitting the user to change or modify aromas as desired, mix one or more aromatic substances depending on the user's preferences and/or to adjust the rate of aroma delivery into the ambient air by controlling the amount or concentration of the aromatic fluid furnished to the substrate, and heat generated by a lit candle associated therewith. In addition, the aroma dispenser is adaptable for use with various types of candles scented or non-scented, and allows for easy replacement of the candle upon exhaustion. The cost effective and efficient manner by which these dispensers are constructed and implemented, makes such dispensers especially suitable for household use.

Figure 1A:
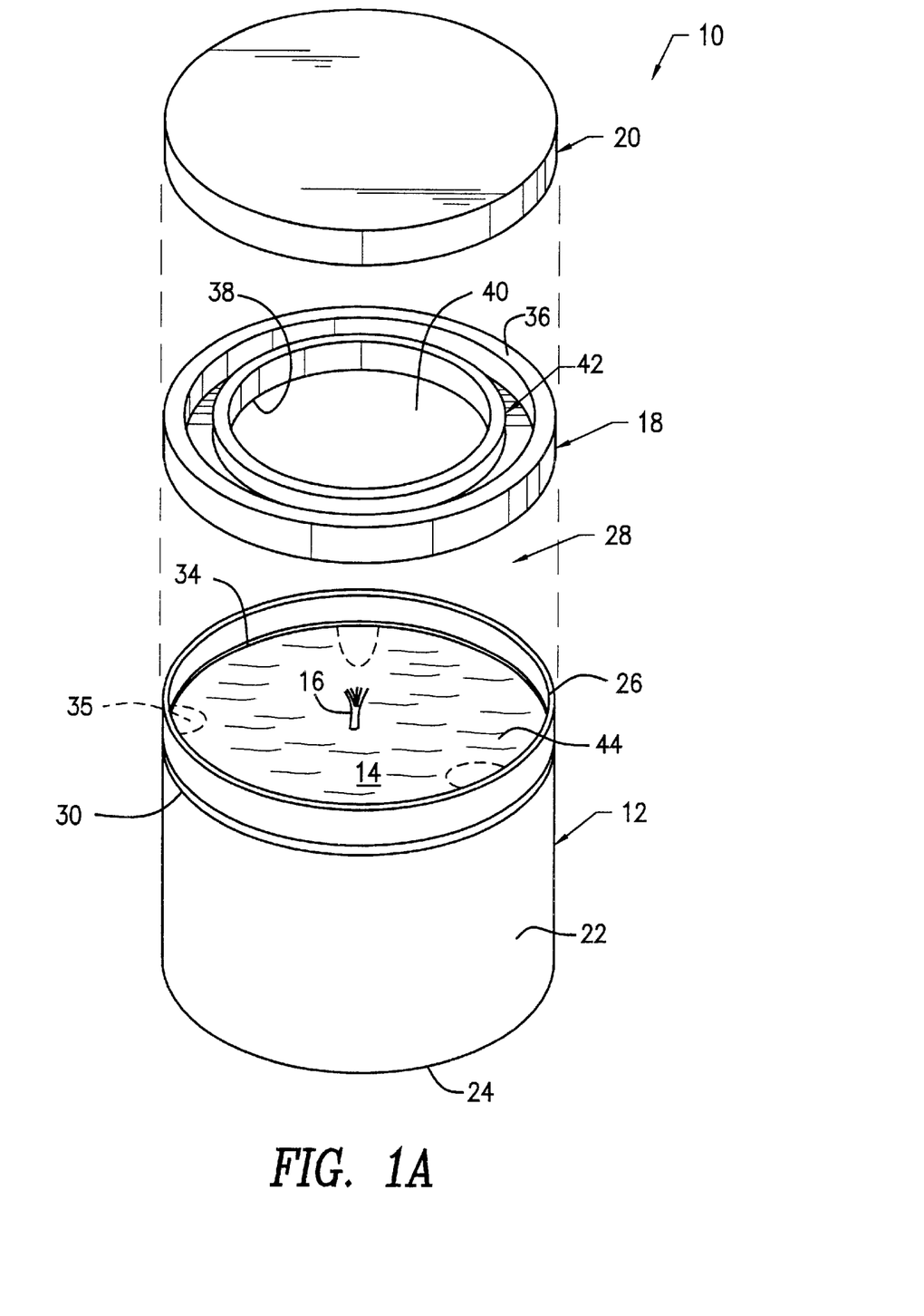
FIG. 1A is an exploded assembly diagram of an aroma dispenser for one embodiment of the present invention.
Figure 1B:
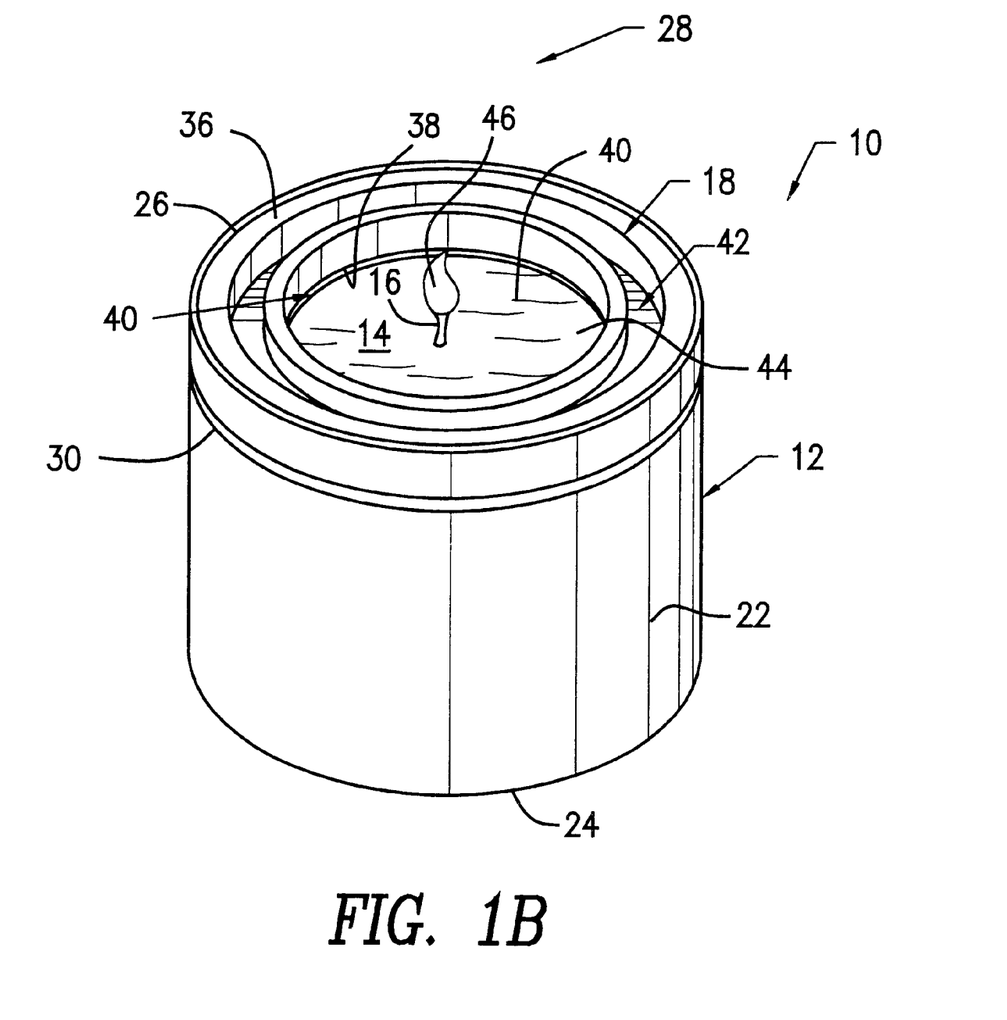
FIG. 1B is a pictorial view of the aroma dispenser of the FIG. 1A with a lit wick.

Referring to FIGS. 1A and 1B, one embodiment of an aroma dispenser 10 of the present invention is shown. The aroma dispenser 10 generally includes a support structure in the form of a container 12, a candle 14 with a centrally located wick 16, an annular, porous substrate 18, and optionally, a lid 20. The container 12 comprises a tubular sidewall 22 with a closed bottom 24 and an opening 26 at a top end 28. The lid 20 is adapted to fit over the container opening 26 to enclose and seal the contents therein. During use, the lid 20 may be used as a candle flame snuffer which is the preferred method of extinguishing the candle 14. It is noted that the shape of the container 12 and the corresponding lid 20 is not limited to the cylindrical configuration shown and may include other shapes and configurations as desired.

A ridge 30 projecting circumferentially around the container 12 is provided for sealing engagement with the lid 20. The container 12 and the lid 20 are composed of a rigid, durable material, preferably having refractory and flame resistant properties including, but not limited to, ceramic, metal, glass, stone, and alumina. The candle 14 is housed within an interior volume 32 formed between the circular sidewall 22 and closed bottom 24, in this example.

The container 12 further includes a radial projection 34 extending along an interior portion of the container sidewall 22 above the candle 14. The radial projection 34 supports and coaxially positions the annular substrate 18 above the candle 14. Alternatively, the container may include a plurality of inwardly extending tabs 35 (shown in FIG. 1A in phantom), preferably three spaced apart tabs 35 for supporting the substrate 18 above the candle 14. The center of the substrate 18 is circular and open, and is coaxially aligned with the wick 16 of the candle 14. The annular substrate 18 includes a top end 36, a bottom end 38, and a relatively large centrally located circular hole 40. A circumferential channel 42 extends along the top end 36 of the substrate 18 for captively retaining a quantity of an aromatic fluid, wherein the substrate 18 effectively absorbs and retains the fluid therein. The substrate 18 is preferably consists of a porous, refractory material including, but not limited to, ceramic, volcanic rock, and earthenware.

The candle 14 is composed of a scented or non-scented wax or paraffin material 44 enclosing a centrally located wick 16 therein. The candle 14 resides within the interior volume of the container 12, in this example. Note that the candle 14 may include other forms such as freestanding candles centrally located within the container 12 and away from the tubular sidewall 22.

Referring specifically to FIG. 1B, the substrate 18 is shown mounted on the radial projection 34 within the container 12. The top end 36 of the substrate 18 is flush with the opening 26 of the container 12. A flame 46 burning at the end of the wick 16 provides heat to the nearby substrate 18 for retaining a quantity of aromatic fluid. Through the heating effect generated by the surrounding ambient air and/or the flame 46 of the candle 14 when lit, portions of the furnished aromatic fluid become vaporized and are released from substrate 18 into the air for dispensing aroma. It is noted that the substrate 18 may include other shapes and configurations which permit the substrate 18 to be retained within the associated container 12, and allows for uniform heating thereof by the centrally located candle flame 46 with the wick 16 lit.

Figure 2:
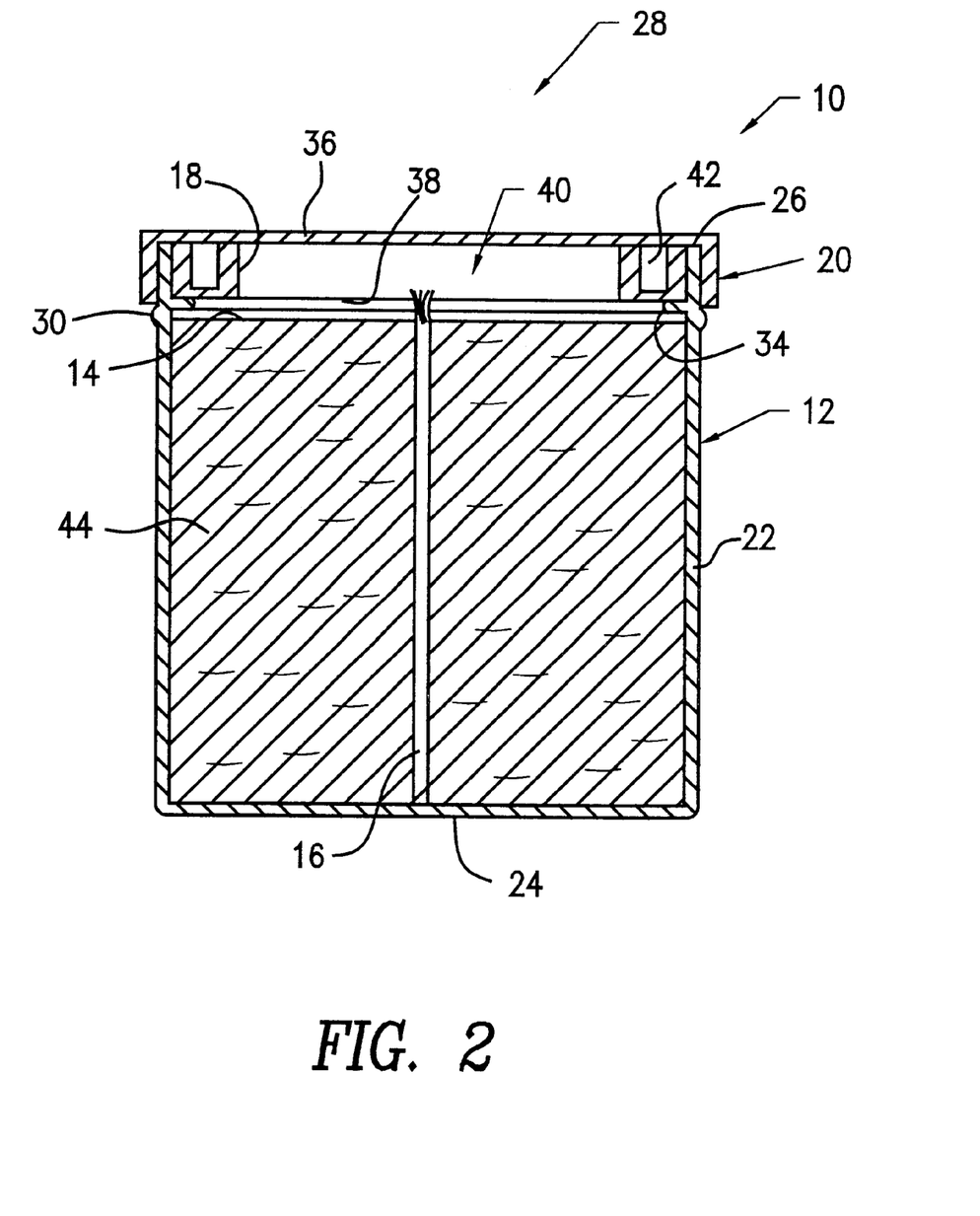
FIG. 2 illustrates a cross-sectional elevational view of the aroma dispenser of FIG. 1A.

Referring to FIG. 2, a cross sectional view of the aroma dispenser 10 is shown with the lid 22 placed over the opening 26 for a sealing the container 12. It is preferred, although not necessary to have a tight frictional fit therebetween via appropriate dimensioning. However, the fit should be such that the lid 20 may facilitatively be removed or changed, if desired.

Figure 3:
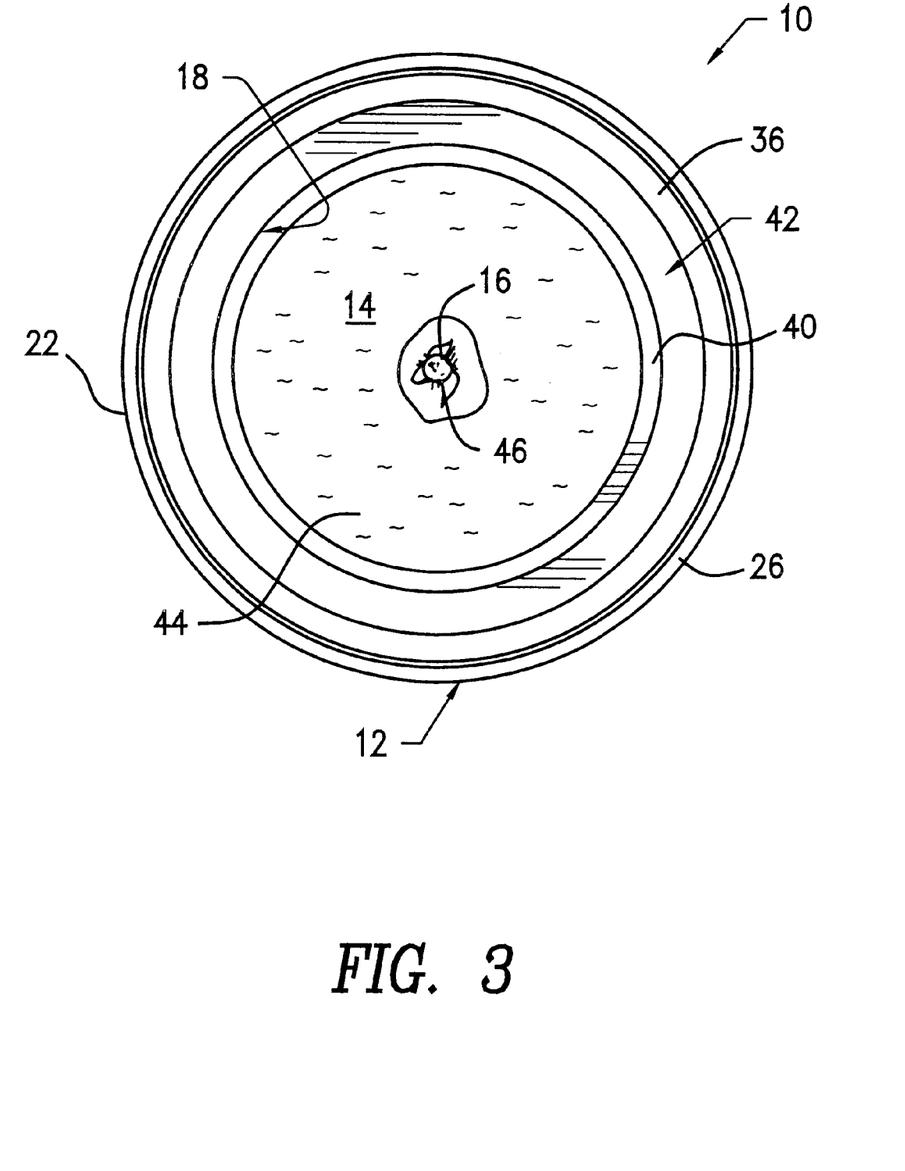
FIG. 3 is a top plan view of the aroma dispenser of FIG. 1B.

Referring to FIG. 3, a top plan view of the aroma dispenser 10 is shown. The wick 16 is located centrally from the substrate 18. The throughhole 40 of the substrate 18 allows the oxygen to reach the flame 46 of lit wick 16, and the combustion products to escape unimpeded. As heat generated by the flame 46 radiates and heats the substrate 18, the inside and bottom surfaces are heated to a temperature which is sufficient to efficiently drive the aromatic fluid out of the substrate 18 in a vaporous form without being consumed or ignited by the flame 46. The substrate 18 is sufficiently spaced away from the flame 46 to provide a safe and clean operation. Moreover, the convective current generated by the flame 46 of the candle 14 further acts to carry the aroma vapors away from the aroma dispenser 10 for desirable diffusion. Under this arrangement, most of the aromatic fluid is efficiently utilized for producing aroma. As noted above, the size and shape of the container 12 may vary according to the user's desire, and the size and shape of the substrate 18 may accordingly be configured to accommodate within the corresponding container's dimensions.

With reference generally to FIGS. 1A through 3, a quantity of a desired aromatic fluid is placed into the channel 42 of the substrate 18. The porous substrate 18 absorbs and retains the aromatic fluid placed therein. Since the aromatic fluid is interspersed within the substrate 18, the danger of the fluid being ignited by the flame is greatly reduced. Heat from the lit wick 16 of the candle 14 causes the retained aromatic fluid to evaporate and diffuse into the ambient air in a safe and efficient manner. Advantageously, the rate of dispersion may be controlled by the user by simply adjusting the concentration of the aromatic fluid or the amount of the aromatic fluid deposited on the substrate 18. When the aromatic fluid in the substrate 18 is exhausted, the user may recharge the substrate 18 with the same aromatic fluid or utilize one or more different aromatic substances in accordance with the user's tastes and desires at the time for flexibility and versatility.

When the wick 16 of candle 14 is lit, the lid 20 may be used as a candle snuffer to put out the flame 46. Once the flame 46 is extinguished the lid 20 may be left on the container 12 to seal the aroma within the substrate 18, or subsequently removed for passively dispensing the aroma into the ambient air for a slower rate of dispersion.

Figure 4A:
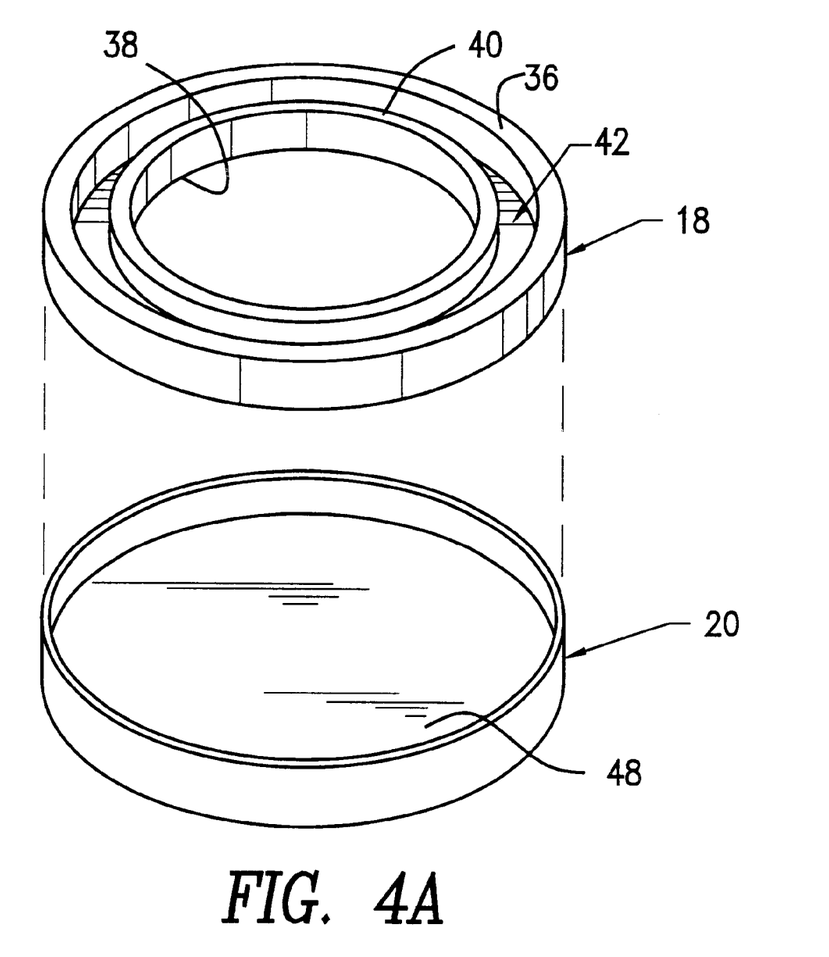
FIG. 4A is an exploded assembly diagram of a substrate shown in FIG. 1A disposed in a lid.
Figure 4B:
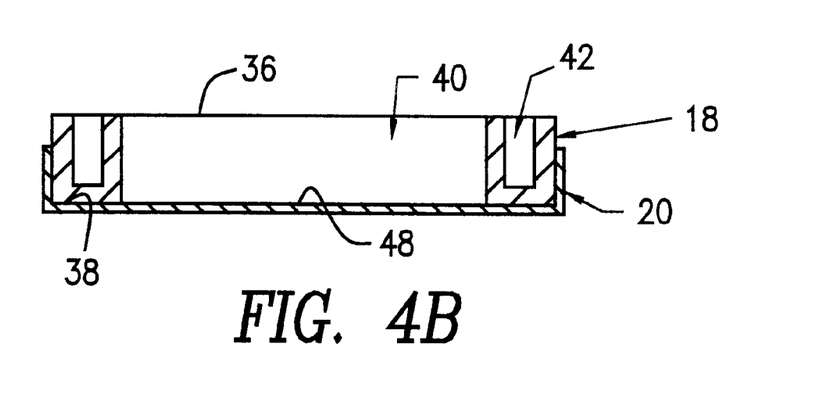
FIG. 4B is a cross sectional view of the substrate and lid shown in FIG. 4A.

Alternatively, as shown in FIGS. 4A and 4B, the aroma dispenser 10 may be arranged for passive diffusion of the aromatic fluid by placing the substrate 18 on an inside surface 48 of the upturned lid 20. In this manner of operation, heat from the ambient air and the vapor pressure of the aromatic fluid in combination, induce slow release and diffusion of the aroma from the substrate 18.

Figure 5A:
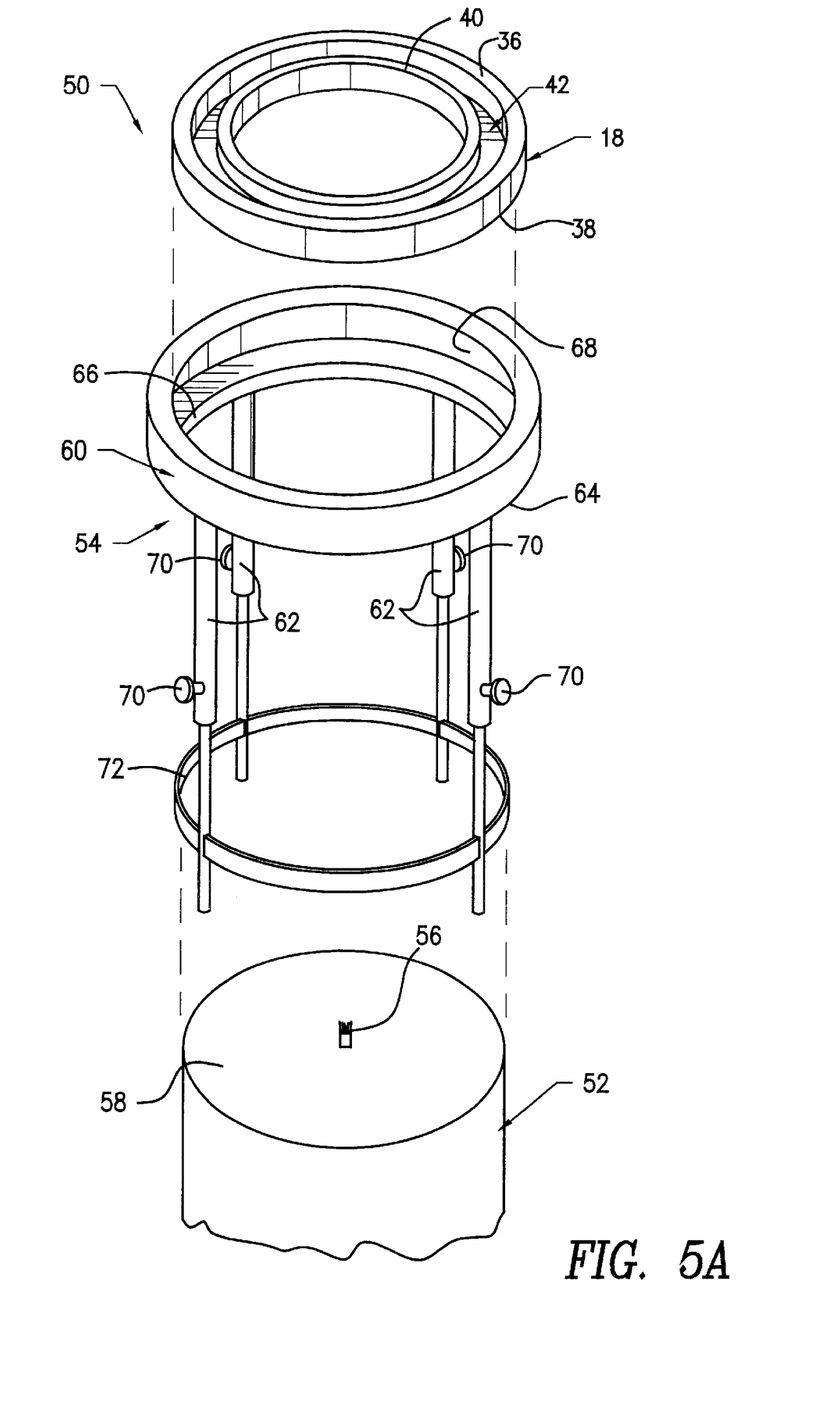
FIG. 5A is an exploded assembly diagram of an aroma dispenser for another embodiment of the present invention.
Figure 5B:
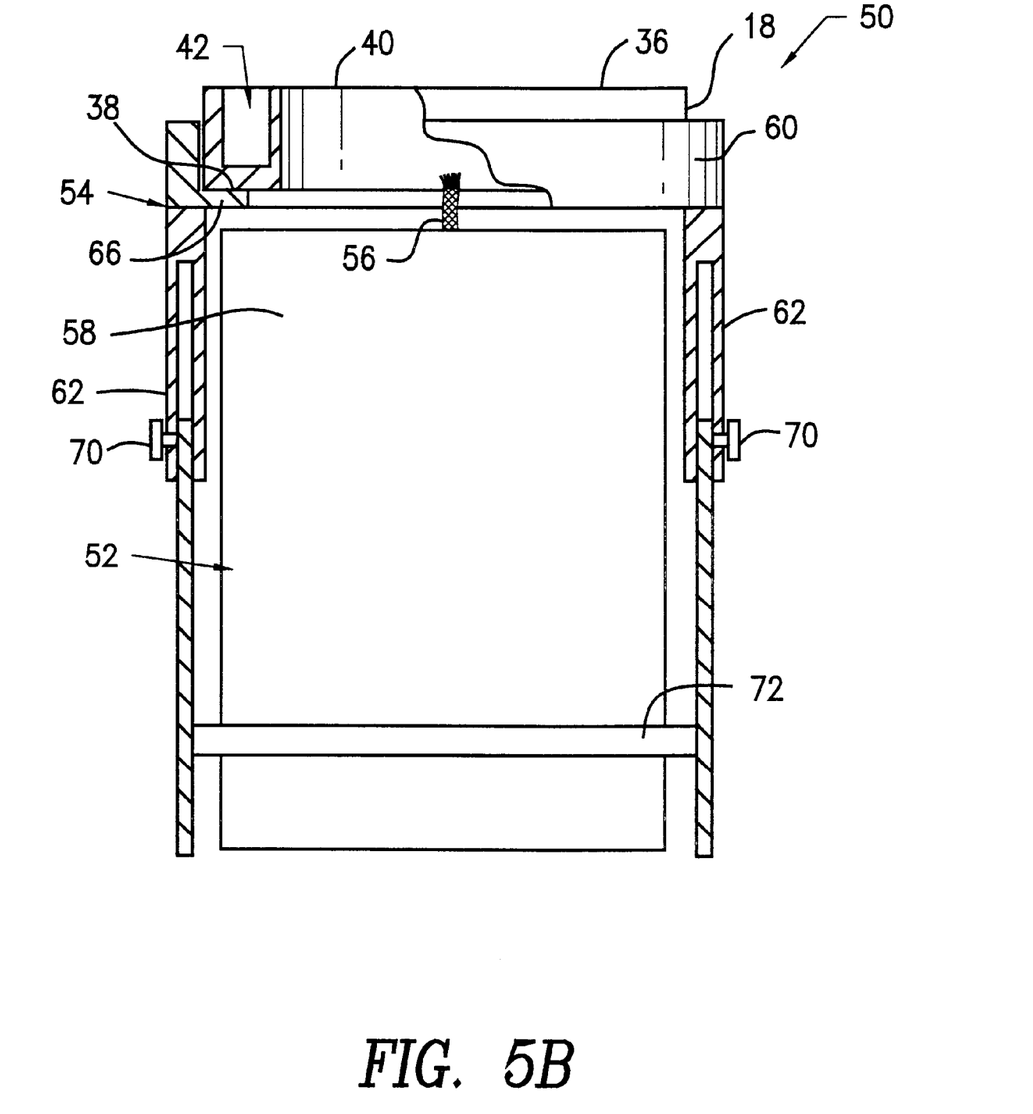
FIG. 5B is a cross sectional view of the aroma dispenser shown in FIG. 5A.

In another embodiment of the invention, an aroma dispenser 50 of the present invention includes a free-standing candle 52 and a support structure 54 for holding the annular substrate 18 over the candle 52. The candle 52 includes a wick 56 embedded in a paraffin-like wax material 58, in this example. The support structure 54 includes a ring portion 60, and a plurality of legs 62 extending downwardly from a bottom surface 64 of the ring portion 60. The bottom end 38 of substrate 18 is supported by a circumferential ledge 66 extending along an inside surface 68 of the ring portion 60. The plurality of legs 62 serve to permit manual positioning of the substrate 18 in a horizontal manner over the candle 52 in proximity to and concentric with the wick 56. The plurality of legs 62 are each telescopically configured to permit adjustment of the height of substrate 18 in relation to the height of the candle 52. A tightening screw 70 is provided on each leg 62 to securely fix the adjusted height of the support structure 54. The support structure 54 further includes a circular rib 72 connecting the lower ends of the legs 62 for structural reinforcement and rigidity. The support structure 54 is preferably consists of a rigid, durable material which is fireproof, such as a metallic material or inflammable plastic, for example. It is further noted that the shape and size of the support structure 54 and the substrate 18 may be varied as desired, and in accordance with a given application or candle size.

Although various embodiments of the invention have been shown and described, they are not meant to be limiting. Those of skill in the art may recognize various modifications to these embodiments, which modifications are meant to be covered by the spirit and scope of the appended claims. For example, the candles and associated substrates 18 can be of any desired and practical shape, including rectangular, polygonal, and so forth or the lid of the container may include other configurations such as including vents for permitting continuous aroma dispensing.

What is claimed is:

1. An aroma dispenser comprising:
    a candle that when lit is a flame source for providing heat;
    an open, porous substrate adapted for absorbing and reversibly retaining a quantity of at least one aromatic fluid therein, said substrate having a bottom; and
    a support structure including at least a plurality of radial projections for removably receiving and holding the bottom of said porous substrate in a spaced-apart relationship at a desired height above said flame source, whereby heat generated by said flame source induces the retained aromatic fluid within the substrate to disperse into the ambient air.

2. The aroma dispenser of claim 1, wherein said candle comprises a wick embedded therein and protruding from a wax material.

3. The aroma dispenser of claim 2, wherein the support structure further comprises:
    a container for holding the candle having at least one sidewall, a closed bottom and an opening at a top end, wherein said plurality of radial projections include a plurality of spaced apart tabs extending radially inward from an inside rim surface of the container proximate the opening for horizontally supporting the bottom of said substrate over said candle with the wick located centrally under said substrate.

4. The aroma dispenser of claim 2, wherein the support structure further comprises:
    a container for holding the candle having at least one sidewall, a closed bottom and an opening at a top end, wherein said plurality of radial projections include a continuous ledge extending radially along an inside rim surface of the container proximate the opening for horizontally supporting the bottom of said substrate over said candle with the wick located centrally under said substrate.

5. The aroma dispenser of claim 4, further comprising a lid being configured for enclosing engagement with the opening of said container for sealing the aromatic fluid therein during non-use, and providing a candle snuffer for extinguishing said candle.

6. The aroma dispenser of claim 5, wherein said lid is adapted for retaining said substrate away from said candle and said container, for passively dispensing aromatic vapors by natural convection of said aromatic fluid.

7. The aroma dispenser of claim 4, wherein said substrate includes a centrally located hole and an outer radial edge conforming to the shape of the container side wall.

8. The aroma dispenser of claim 7, wherein the sidewall of said container is circular to provide a cylindrical shape.

9. The aroma dispenser of claim 7, wherein the sidewall of said container is rectangularly shaped.

10. The aroma dispenser of claim 7, wherein the side wall of said container is polygonally shaped.

11. The aroma dispenser of claim 1, wherein the substrate includes a centrally located hole.

12. The aroma dispenser of claim 1, wherein said substrate is annular or ring shaped.

13. The aroma dispenser of claim 12, wherein the substrate further includes a circumferential channel extending along a top surface thereof.

14. The aroma dispenser of claim 1, wherein said open, porous substrate comprises a ceramic material.

15. The aroma dispenser of claim 1 wherein said substrate and support structure consists of refractory and flame resistant material.

16. The aroma dispenser of claim 1, wherein the substrate is annularly shaped, and said support structure comprises an annular base member, and a plurality of legs each extending from a bottom portion of said annular member, wherein said plurality of radial projections include a ledge extending radially along an inside surface of said member for holding said substrate above said flame source in a coaxial manner.

17. The aroma dispenser of claim 16, wherein said plurality of legs are telescopically adjustable for reversibly extending said plurality of legs.

18. An aroma dispenser comprising:
a container housing a candle with a centrally located wick, said container including a cylindrical sidewall portion with a closed base, and an open top;
an open, porous annular substrate of refractory material, said substrate being configured for absorbing and reversibly retaining a quantity of at least one vaporizable aromatic fluid, and for being suspended by a support element extending radially inward from an inside rim portion of the container sidewall proximate the open top of the container for positioning the substrate coaxially above and with the candle wick; and
a lid adapted for enclosing said substrate and candle within said container to prevent dispersal of said aromatic fluid during non-use, and to extinguish said candle during use.

19. The aroma dispenser of claim 18, wherein the support element is a radial ledge.

20. The aroma dispenser of claim 18, wherein the support element is a plurality of spaced apart tabs.

21. An aroma dispenser comprising:
an annular platform oriented horizontally, said platform being supported by a plurality of legs extending therefrom, said plurality of legs being telescopic for selectively adjusting the height of the platform and the substrate above said candle;
a candle consisting of a paraffin-like material with a centrally located wick therein, said candle being located underneath said platform in a spaced away manner, and
an annular ceramic substrate adapted for absorbing and releasably retaining a quantity of at least one aromatic fluid therein, said substrate being adapted for suspension by said platform above said candle and coaxial therewith.

22. The aroma dispenser of claim 21, wherein said platform and plurality of legs are each composed of an inflammable material.

* * * * *